(12) United States Patent
Mouraret et al.

(10) Patent No.: US 11,284,686 B2
(45) Date of Patent: Mar. 29, 2022

(54) PERFUME DIFFUSION DEVICE IN A PORTABLE JEWEL

(71) Applicant: SILGAN DISPENSING SYSTEMS LE TREPORT, Le Treport (FR)

(72) Inventors: Guillaume Mouraret, Paris (FR); Emir Ezzina, Montigny-le-Bretonneux (FR)

(73) Assignee: SILGAN DISPENSING SYSTEMS LE TREPORT, Le Treport (FR)

( * ) Notice: Subject to any disclaimer, the term of this patent is extended or adjusted under 35 U.S.C. 154(b) by 266 days.

(21) Appl. No.: 16/510,927

(22) Filed: Jul. 14, 2019

(65) Prior Publication Data

US 2020/0015556 A1 Jan. 16, 2020

(30) Foreign Application Priority Data

Jul. 13, 2018 (FR) ...................................... 1856461

(51) Int. Cl.
*A44C 15/00* (2006.01)
*A45D 34/04* (2006.01)
*A01M 1/20* (2006.01)
*A45D 34/00* (2006.01)

(52) U.S. Cl.
CPC ......... *A44C 15/002* (2013.01); *A01M 1/2044* (2013.01); *A45D 34/04* (2013.01); *A45D 2034/007* (2013.01)

(58) Field of Classification Search
CPC .. A44C 15/002; A44C 25/002; A01M 1/2044; A45D 34/04; A45D 2034/007; A45D 2034/002; A45D 34/02; A61L 2209/133; A61L 9/127
See application file for complete search history.

(56) References Cited

U.S. PATENT DOCUMENTS 5,725,152 A 3/1998 Akyu
7,441,755 B2 * 10/2008 O'Leary ............. A01M 1/2044
261/104

FOREIGN PATENT DOCUMENTS

JP 3088277 * 6/1997 ............. A61L 9/127
JP 2016078935 5/2016
WO WO2006/061803 6/2006

OTHER PUBLICATIONS

English translation of JP3088277 (Year: 1997).*

* cited by examiner

*Primary Examiner* — Qingzhang Zhou
*Assistant Examiner* — Joel Zhou (57) ABSTRACT

A device for diffusion of a liquid product, of the perfume type, stored in a reservoir includes at least one fixed part capable of being mounted on the reservoir, and offering at least one point of product supply by capillarity, the fixed part including a fixed porous body capable of being impregnated with product by capillarity by being directly immersed in the reservoir. The device also includes a nomadic element for each supply point, including a mobile porous body capable of being impregnated with product by capillarity while being in contact with the fixed porous body when the nomadic element is mounted on the fixed part. The nomadic element also includes a decorative structure of the jewel type, the mobile porous body being housed inside the decorative structure.

6 Claims, 7 Drawing Sheets

PERFUME DIFFUSION DEVICE IN A PORTABLE JEWEL

CROSS REFERENCE TO RELATED APPLICATIONS

This application claims priority under 35 U.S.C. § 119(a) to French Patent Application Serial Number 1856461, filed Jul.13, 2018, the entire teachings of which are incorporated herein by reference.

BACKGROUND OF THE INVENTION

Field of the Invention

The invention relates to a device for diffusion of a liquid product, such as a cosmetic product, more particularly a perfume or an eau de toilette, that is stored in a reservoir. The invention also relates to a vial including a reservoir wherein the product is stored, and including such a product diffusion device.

Description of the Related Art

Home perfume diffusers are known. These diffusers are not designed to be moved; they are fixed.

Perfume diffusers for the skin are also known, consisting of porous elements intended to be impregnated with perfume and then applied to the skin. Yet, some people do not want to directly apply perfume onto their skin or clothes, for example because of allergies, or because some perfumes can stain clothes.

In this case, there are perfume diffuser jewels that the user can wear on himself during the day. For example, they consist of a pendant encapsulating a piece of fabric that the user dips into the perfume before closing the pendant. This prevents contact between the perfume and the skin of the user, as well as his clothes.

The disadvantage resides in the succession of steps to be carried out, in this case, opening the pendant, spraying perfume on the piece of fabric, positioning the fabric in the pendant, closing the pendant. All this causes weariness for the user, and non-suitability of the product. Moreover, perfume present on the fabric comes into contact with the pendant and causes a chemical reaction affecting the material of the pendant, such as corrosion, etc.

BRIEF SUMMARY OF THE INVENTION

The present invention aims to overcome the different disadvantages mentioned above, by means of a diffusion device enabling to diffuse perfume throughout the day via a nomadic element carried by the user, that can easily be refillable with perfume with a minimum of steps, and that is not likely to be altered by a chemical reaction with the perfume. This aim is achieved thanks to a diffusion device of a liquid product, of the perfume type, stored in a reservoir, including:
  at least one fixed part capable of being mounted on the reservoir, and offering at least one point of product supply by capillarity, the fixed part including a fixed porous body capable of being impregnated with product by capillarity by being directly immersed in the reservoir;
  a nomadic element for each supply point, including a mobile porous body capable of being impregnated with product by capillarity while being in contact with the fixed porous body when the nomadic element is mounted on the fixed part, the nomadic element also including a decorative structure, of the jewel type, the mobile porous body being housed inside the decorative structure, the nomadic element including means for withdrawing the mobile porous body with respect to the decorative structure to prevent any direct contact between them.

In accordance with an embodiment of the invention two porous bodies are provided—one fixed, immersed in the reservoir for drawing off perfume, and the other integrated, mobile within a nomadic element that the user can carry. Placing these two porous bodies in contact enables to transfer, by capillarity, the perfume from the reservoir to the nomadic element. It is therefore not necessary to disassemble the nomadic element to have access to a porous element that then needs to be dipped in the reservoir. In the present invention, no element is to be disassembled. It is sufficient to deposit the nomadic element on the supply point thereof, so as to put the two porous bodies in contact and that the transfer of perfume takes place.

In addition, the porous body is housed inside the decorative structure, which means that the user does not touch the mobile porous body when they handle the nomadic element. Therefore, there is no contact between the user's skin and the mobile porous body.

Finally, the mobile porous body is not in contact with the decorative structure. Indeed, it is withdrawn, such that the perfume impregnated in the mobile porous body does not touch the decorative structure, and does not alter it.

The diffusion device may include one single fixed part mounted on the reservoir. Alternatively, the diffusion device can include several fixed parts mounted on the same reservoir. For example, the reservoir can have several necks, each neck receiving a fixed part.

Each fixed part can present a single supply point to refill product in a nomadic element. Alternatively, each fixed part can have several supply points to refill product in several nomadic elements.

According to the different embodiments of the invention, that can be taken together or separately:
  the fixed part includes a fixing base on the reservoir retaining the fixed porous body in a state of compression, the base being perforated by slits through which decompressed projections from the fixed porous body project. Parts of the fixed porous body facing the slits tend to engage into the slits and therefore to decompress forming projections, or domes.
  the base includes a sleeve closed by a cap at the top and open at the bottom so as to define a housing for the fixed porous body, the slits being formed on the peripheral wall of the sleeve. The fixed porous body is inserted in the sleeve via the lower opening, and is held in position within the sleeve by compression.
  the fixed porous body advantageously presents a diffusion head housed in the top part of the sleeve, and a supply rod that dips into the reservoir to come into contact with the product, and to bring it to the head by capillarity.
  the base includes a skirt that develops around the bottom part of the sleeve, the skirt including means of fixing to the neck of the reservoir. For example, the skirt click fits into the neck of the reservoir. It can also have in inner thread to be screwed into the neck of the reservoir. Other fixing systems can be considered.
  the fixed part includes means of protection against the evaporation of the product through the slits. The product contained in the fixed porous body diffuses through the slits. Thus, the reservoir can be emptied by diffusion even when there is no nomadic element positioned on the fixed part. It is thus essential to ensure a sealing around the fixed porous body, that is impregnated under all circumstances, when the nomadic element is not in position on the fixed part.

the means of protection against the evaporation of the product consist of a fret that is movable in translation against spring means between an upper protection position facing the slits and a lower position providing free access for the nomadic element to the slits. When the fret is in the upper position, it surrounds the sleeve and obstructs all the slits. The sealing of the fixed porous body is ensured.

the spring means of the fret consist of flexible tabs resting at the bottom of a groove formed between the sleeve and the skirt of the base. The fret can move from the upper position to the lower position by bending/deformation of the tabs.

the cap includes a peripheral rim against which the fret abuts in the upper position to ensure the sealing between the base and the fret when the nomadic element is not in place on the fixed part. The flexible tabs tend to lift the fret into the upper position when they are no longer solicited. The fret then rises up to come into contact with the peripheral rim of the cap. Thus, the fret abuts under the rim, and blocks any entry/exit of air with respect to the sleeve, so as to prevent the diffusion of perfume already impregnated on the fixed porous body.

the mobile porous body consists of an annular element surrounding the perforated peripheral wall of the sleeve when the nomadic element is in place on the fixed part, the nomadic element applying a force on the fret so as to hold it in the lower position by the effect of friction. When the user pushes the nomadic element onto the fixed part, the nomadic element pushes on the fret and moves it from the upper position to the lower position, against the spring means. The nomadic element is then held in position on the fixed part thanks to the axial and radial friction between it and the sleeve. Indeed, the inner diameter of the nomadic element is sized with respect to the outer diameter of the sleeve, such that pushing of the nomadic element onto the sleeve involves sufficient friction such that it remains in position on the fixed part in the short term and in the long term, if necessary. The flexible tabs are not powerful enough to raise the fret when the nomadic element is in place. As an alternative, the nomadic element can be held in position on the fixed part by click-fitting.

the means of withdrawal of the mobile porous body with respect to the decorative structure of the nomadic element consist of a crown supporting the mobile porous body, the crown being removably fixed in the decorative structure.

the mobile porous body is placed inside the crown, the mobile porous body coming directly into contact with the decompressed projections from the fixed porous body when the nomadic element is in place on the fixed part.

the mobile porous body is arranged outside the crown, the crown being perforated with openings through which portions of the mobile porous body are accessible, the decompressed projections from the fixed porous body coming into contact with these portions of the mobile porous body when the nomadic element is in place on the fixed part.

the crown includes an upper attachment lip and a lower attachment lip for the fixing thereof with the decorative structure, the lips having a radial extension sized so as to ensure that the mobile porous body is withdrawn with respect to the decorative structure. Thus, there is no contact between the mobile porous body and the decorative structure, to avoid any deterioration of the decorative structure.

the sleeve includes tabs extending tangentially from the outer peripheral wall thereof and being all oriented in the same direction of rotation, each tab being arranged between two adjacent slits, each tab being capable of penetrating inside an opening in the crown when the nomadic element is in place on the fixed part and the user rotates the nomadic element. Thus, the crown can be attached onto the base and the user can easily separate the decorative structure from the crown, in order to replace the mobile porous body;

the lower and upper attachment lips of the crown are adapted to fold back on the mobile porous body by elastic radial deformation of the crown at the end of the tabs being click-fitted in the openings, to separate the crown from the decorative structure.

The invention also relates to a vial including a reservoir capable of storing a fluid product, of the perfume type, and including a diffusion device such as described above.

Additional aspects of the invention will be set forth in part in the description which follows, and in part will be obvious from the description, or may be learned by practice of the invention. The aspects of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE SEVERAL VIEWS OF THE DRAWINGS

The accompanying drawings, which are incorporated in and constitute part of this specification, illustrate embodiments of the invention and together with the description, serve to explain the principles of the invention. The embodiments illustrated herein are presently preferred, it being understood, however, that the invention is not limited to the precise arrangements and instrumentalities shown, wherein.

DETAILED DESCRIPTION OF THE INVENTION

Figure 1:
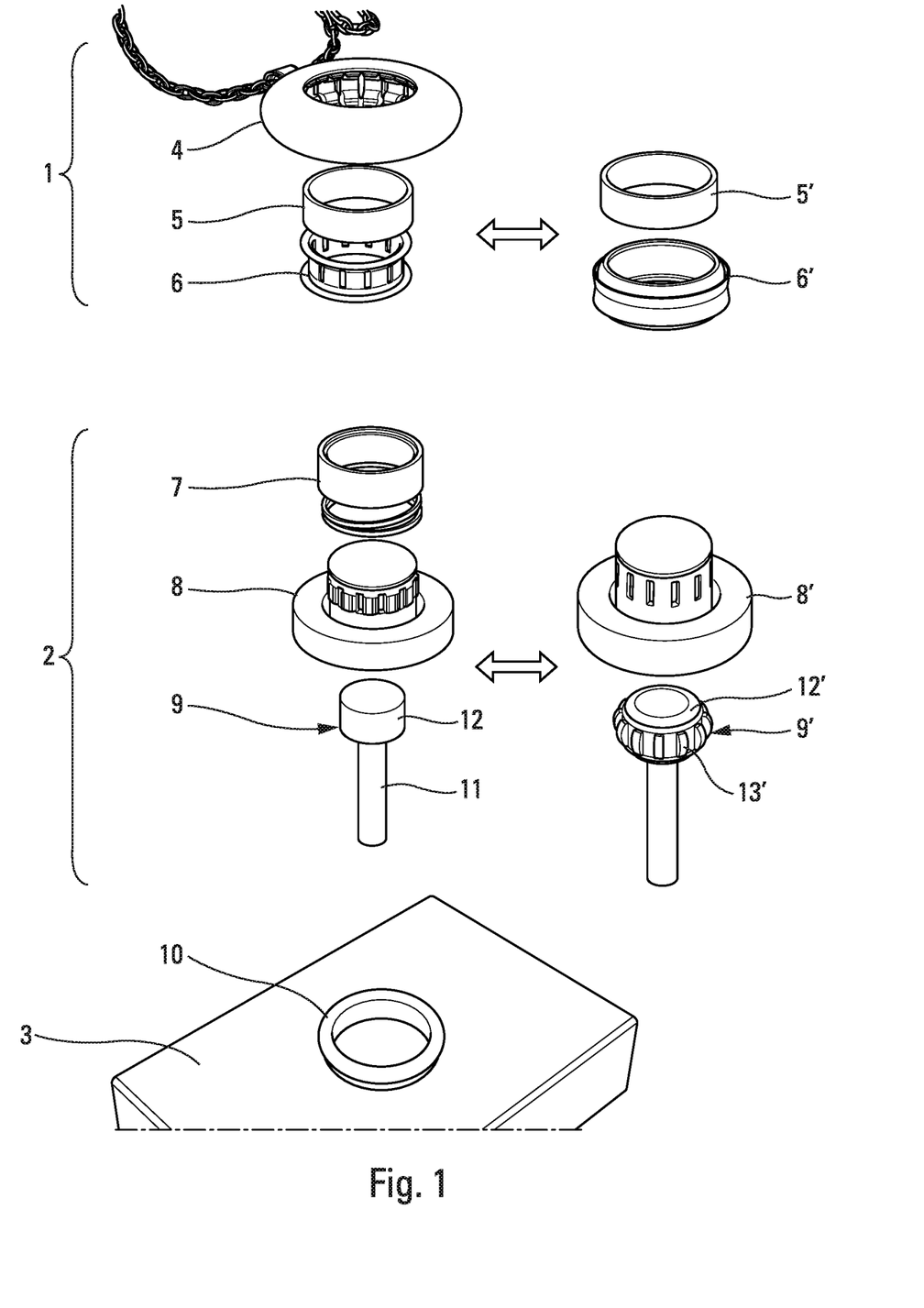
FIG. 1 is an exploded view of the diffusion device according to the invention, with a few variants of the proposed parts on the right.

With reference to FIG. 1, the diffusion device according to the invention is composed principally of a nomadic element 1 capable of being mounted on a fixed part 2, that is itself mounted on a reservoir 3.

This reservoir 3 contains a liquid product that consists of a cosmetic product, and more particularly a perfume or an eau de toilette.

This reservoir 3 has a neck 10 defining an upper opening wherein a porous body of the fixed part 2 of the diffusion device, thus called a fixed porous body 9, can be inserted. This fixed porous body 9 extends over the entire height of the reservoir 3 such that it can touch the bottom of the reservoir 3 to become impregnated with product, regardless of the product filling level in the reservoir 3.

This fixed porous body 9 is fitted into a base 8 of the fixed part 2, capable of being mounted on the neck 10 of the reservoir 3. A fret 7, of which the operation will be described later in the description, also forms part of the fixed part 2.

The nomadic element 1 itself consists mainly of a portable jewel 4 that a user can wear all day, of the pendant type, that diffuses the same perfume as that contained in the reservoir 3. For this, the nomadic element 1 also includes a porous body called the mobile porous body 5. This mobile porous body 5 can be impregnated with perfume when it is brought into contact with the fixed porous body 9, during perfume refill periods. This mobile porous body 5 diffuses perfume by evaporation all day long.

A crown 6 also forms part of the nomadic element 1, in order to support the mobile porous body 5 and to keep the latter at a distance from the jewel 4, such that the perfume present on the mobile porous body 5 does not come into contact with the structure of the jewel 4 so as not to alter it, in particular in terms of corrosion, for example.

In this FIG. 1, some parts of the nomadic element 1 and some part 2 can have variant shapes, the functions thereof remaining identical. These variants represented on the right are numbered with "prime numbers", for more clarity.

In the embodiment presented here, the nomadic element 1 is therefore mainly composed of three annular shaped parts, namely a decorative structure 4 of the jewel type, a mobile porous body 5, and a crown 6. The jewel 4 is, for example, of an O-ring shape.

In the first variant, the mobile porous body 5 is force-fitted all around the crown 6 and then the crown 6/mobile porous body 5 assembly is fitted inside the jewel 4. The crown 6 thus provides an aesthetic function, because it makes it possible to conceal the mobile porous body 5 when the user looks at the centre of the jewel 4.

In the second variant, the mobile porous body 5' is mounted inside the crown 6', then the crown 6'/mobile porous body 5' assembly is mounted inside the jewel 4.

Figure 7:
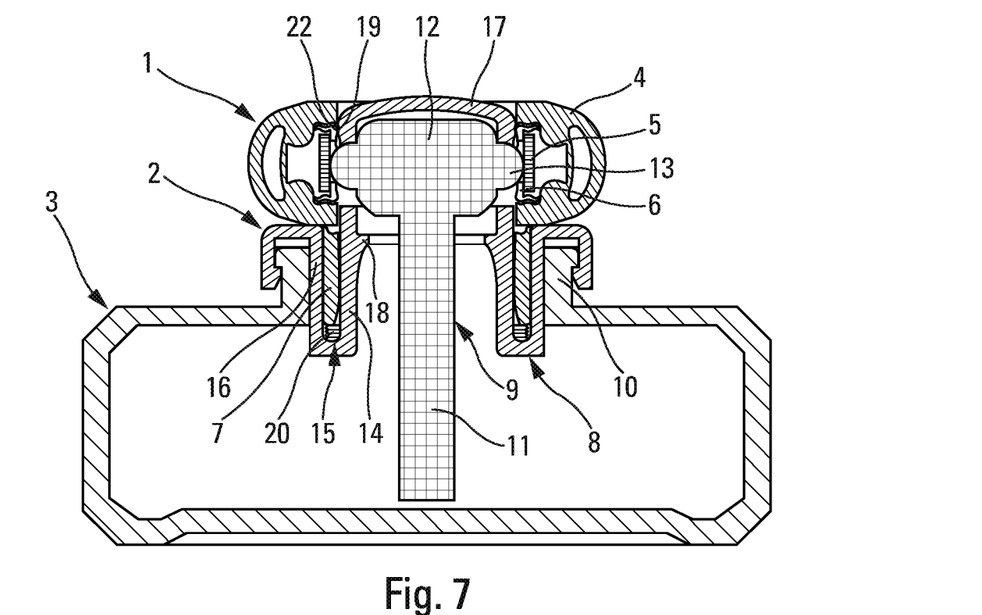
FIG. 7 is a cross-sectional view of the nomadic element mounted on the fixed part.
Figure 8:
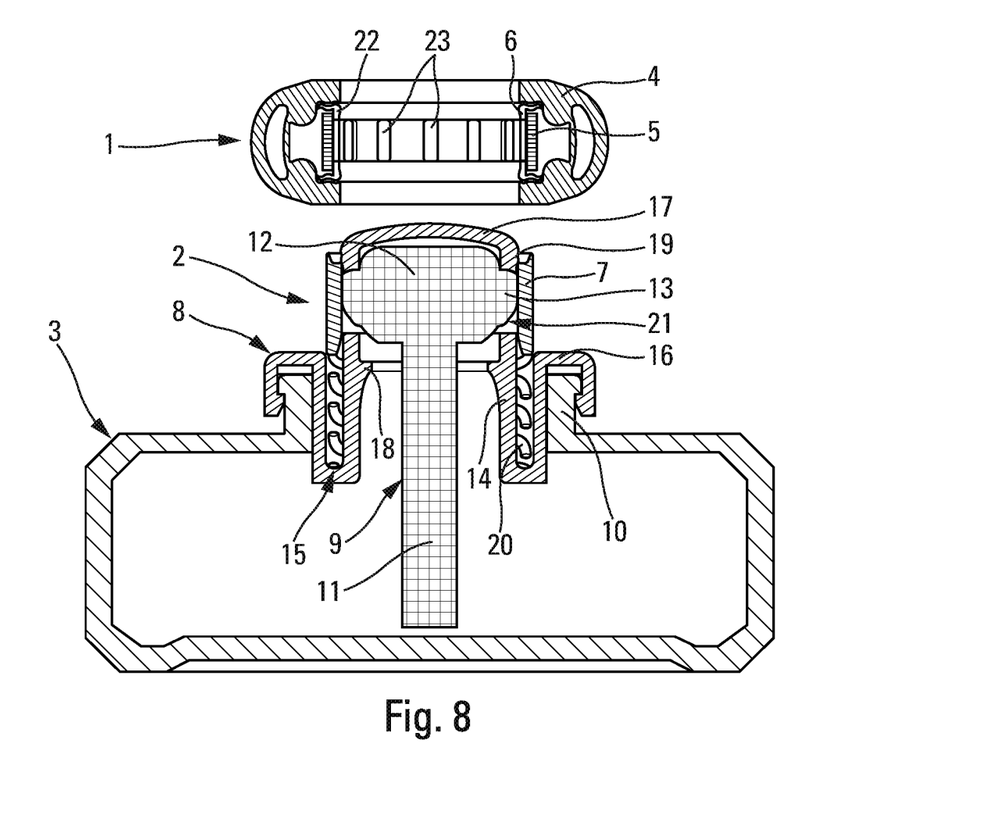
FIG. 8 is a cross-sectional view of the nomadic element at a distance from the fixed part.
Figure 9:
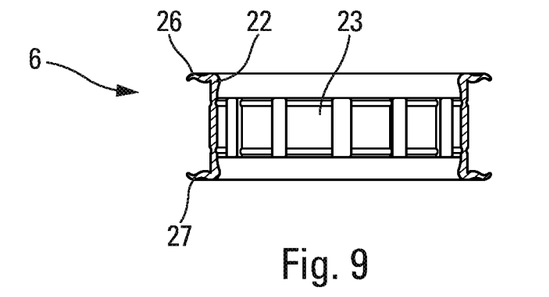
FIG. 9 represents a first possible configuration of a crown belonging to the nomadic element.

In both cases, the crown 6, 6' ensures the function thereof of supporting the mobile porous body 5, 5', and the function thereof to withdrawing the mobile porous body 5, 5' with respect to the jewel 4 to prevent any contact between them. For this, as illustrated in FIGS. 7, 8 and 9, the crown 6 includes an upper attachment lip 26 and a lower attachment lip 27 for the fixing thereof with the jewel 4.

In the first variant, the mobile porous body 5 is pressed against the peripheral wall of the crown 6, and finds itself positioned between these two lips 26, 27. These two lips 26, 27 have a radial extension greater than the thickness of the mobile porous body 5 such that they cover it entirely and such that the latter cannot touch the jewel 4. This radial extension is similar to a cantilever sized so as to keep a certain distance between the mobile porous body 5 and the jewel 4. The jewel 4 itself includes an annular hollow part wherein the crown 6 is inserted. This hollow part is sized so as to form a sufficiently large housing to avoid all contact with the mobile porous body 5.

In the second variant, the mobile porous body 5' is inside the crown 6', thus this crown acts as a barrier between the mobile porous body 5' and the jewel 4.

In both cases, the mobile porous body 5 must be accessible from inside the jewel 4 for the perfume refill thereof. Thus, in the first variant, the crown 6 has openings 23 regularly distributed around the entire periphery thereof. Portions of mobile porous bodies (5) are therefore accessible through the openings 23. The thickness of the mobile porous body 5 is sized so that the portions arranged facing the openings 23 do not project towards the inside of the nomadic element 1. Thus, when taking charge of the nomadic element 1, there is no risk of contact between the skin of a user's fingers and the portions of the mobile porous element 5, or between clothing and the portions of the mobile porous element 5. In the second variant, since the mobile porous body 5' is mounted inside the crown 6', it is directly accessible in the entirety thereof.

Below in the description, the first variant will be revisited by the figures. It must be noted that the second variant could have been selected in the same manner.

Figure 2:
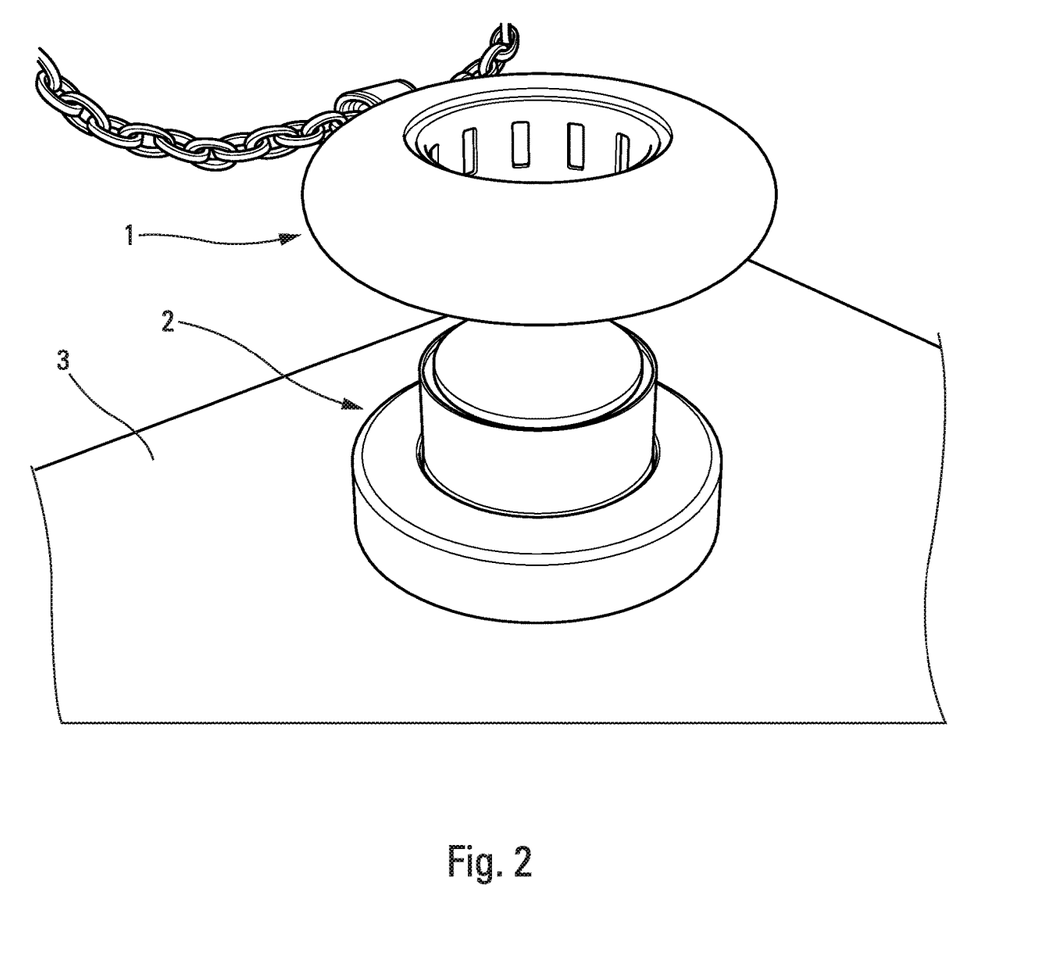
FIG. 2 is a perspective view of a nomadic element ready to be mounted on a fixed part of the diffusion device according to FIG. 1.

In FIG. 2, the nomadic element 1 is fully assembled. In the same way, the fixed part 2 is fully assembled and fixed on the neck 10 of the reservoir 3. This fixed part 2 has one single supply point. The nomadic element 1 is at a distance from this supply point and is ready to be refilled.

Figure 3:
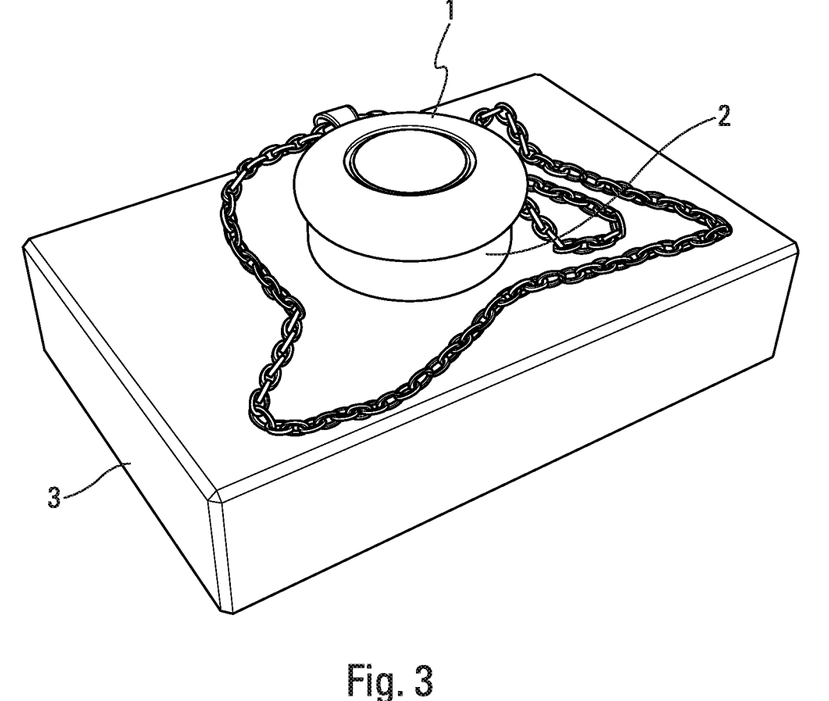
FIG. 3 shows, in perspective, the nomadic element mounted on the fixed part according to FIG. 2.

In FIG. 3, the nomadic element 1 is mounted on the single supply point of the fixed part 2 and is currently being refilled with perfume. In this FIG. 3, there is only one fixed part 2, with one single supply point, to refill one single nomadic element 1.

Figure 4:
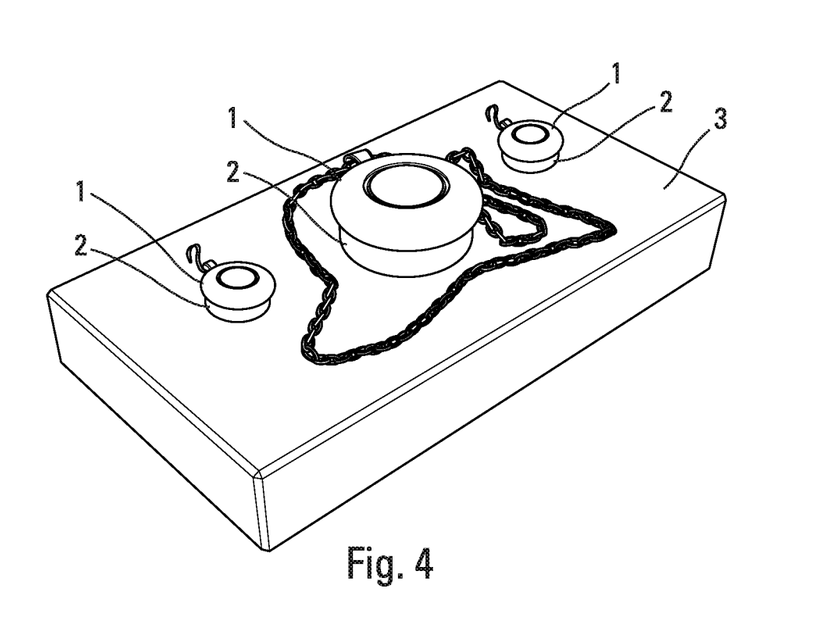
FIG. 4 illustrates three fixed parts on which three nomadic elements can be mounted.

Alternatively, as illustrated in FIG. 4, it is possible to set up three fixed parts 2 on one single reservoir 3, each having one single supply point, so as to be able to refill three nomadic elements 1 simultaneously. In the example illustrated, there is one pendant and two earrings that can be refilled simultaneously, forming part of one single decoration of jewel 4.

Alternatively, it is also possible to provide a fixed part 2 with several supply points in order to be able to refill several nomadic elements 1 simultaneously starting from one single fixed part 2. In this case, either there is one single fixed porous body 9 inserted through one single neck 10 that is divided into several branches then providing several supply points, or there are several fixed porous bodies 9 projecting from the reservoir 3 then providing several supply points.

Figure 6:
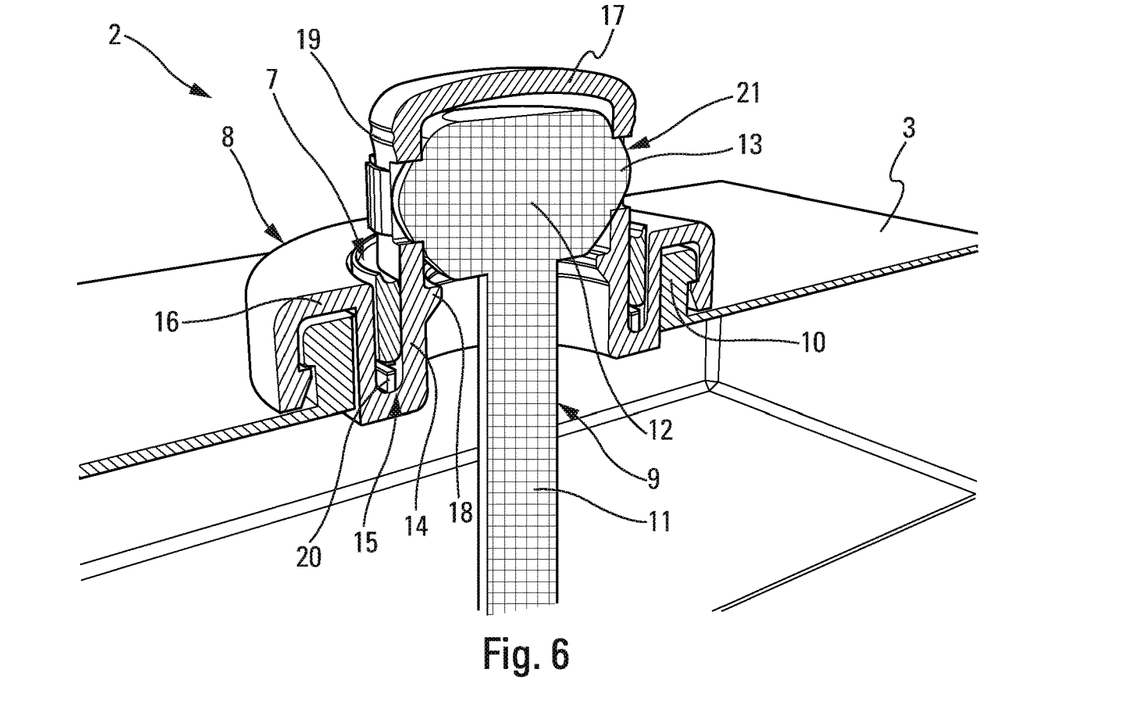
FIG. 6 is a cross-sectional and perspective view of a fixed part with the fret thereof in the lower free access position, mounted on a reservoir.

More specifically, as illustrated in FIG. 6, the fixed part 2 of the diffusion device includes an attachment base 8 on the reservoir 3. This base 8 includes a central sleeve 14 closed in the upper part by a cap 17 and open in the lower part. This sleeve 14 defines an inner housing for the fixed porous body 9. Indeed, the fixed porous body 9 is forced into this sleeve 14 and is in a compression state. More precisely, the fixed porous body 9 includes a head 12 inserted inside the housing as defined above, and from which extends a rod 11 sufficiently long to reach the bottom of the reservoir 3. The fixed porous body 9 is held in position in the housing thanks to compression of the head 12 thereof in the housing, and using an annular rim 18 formed on the inner surface of the sleeve 14, that retains the head 12 if it descended.

The peripheral wall of the sleeve 14 is perforated in the upper part by slits 21 through which decompressed projections 13 lead out from the fixed porous body 9. Indeed, since the latter is compressed, it tends to be swallowed inside the slits 21 in order to expand.

In the first variant illustrated in FIG. 1, the head 12 of the fixed porous body 9 has a regular surface before it is inserted into the sleeve 14, then this head is deformed by compression after insertion, leading to these projections 13 that are swallowed by the slits 21.

In the second variant illustrated in FIG. 1, the head 12' of the fixed porous body 9' has an irregular surface before it is inserted into the sleeve 14. Indeed, it already includes projections 13' cut in advance in the porous mass. These projections 13' are distributed regularly around the head 12', respecting the dimensions and distances of the slits 21 provided for this purpose in the sleeve 14 of the base 8', such that each projection 13' can penetrate inside a corresponding slit 21. These projections 13' are necessarily decompressed because no force is applied to them. This second variant does not prevent compression of the fixed porous body 9' inside the sleeve 14.

Revisiting FIG. 6, the base 8 includes a skirt 16 developing around the lower part of the sleeve 14. This skirt 16 includes means of fixing to the neck 10 of the reservoir 3. In this case, the skirt 16 has an annular return capable of engaging with an annular shoulder provided on the neck 10 of the reservoir 3, so as to ensure an elastic interlocking between the skirt 16 and the neck 10 of the reservoir 3.

When this fixed part 2 is thus mounted on the neck 10 of the reservoir 3, the fixed porous body 9 is automatically impregnated with perfume present inside the reservoir 3. Firstly, perfume enters the rod 11 and then goes up by capillarity to the head 12 of the fixed porous body 9. Thus, the projections 13 from the fixed porous body 9 coming out from the slits 21 of the base 8 are all impregnated with perfume. It is then sufficient to put the nomadic element 1 into place on the upper part of the sleeve 14, such that the nomadic element 1 surrounds all the slits 21 of the sleeve 14, as can be seen in FIG. 7. Thus, the projections 13 from the fixed porous body 9 impregnated with perfume, come into contact with the mobile porous body 5 that has dried out after a day of diffusion, or at least into contact with portions of the mobile porous body 5 accessible via the openings 23 in the crown. By capillarity, the perfume passes from the fixed porous body 9 to the mobile porous body 5.

Preferably, the user puts their jewel 4 into place on the base 8 in the evening at bedtime, such that the refill takes place during the night, and the jewel 4 will be once again ready for use and impregnated with perfume the next morning.

When there is no nomadic element 1 in place on the base 8, the slits 21 and the projections 13 from the fixed porous body 9 are exposed to open air. Consequently, the perfume is permanently diffused in ambient air from the fixed part 2. To prevent this diffusion, and that the tank 3 does not empty in this way, it is necessary to provide means of protection against the evaporation of the product.

Figure 5:
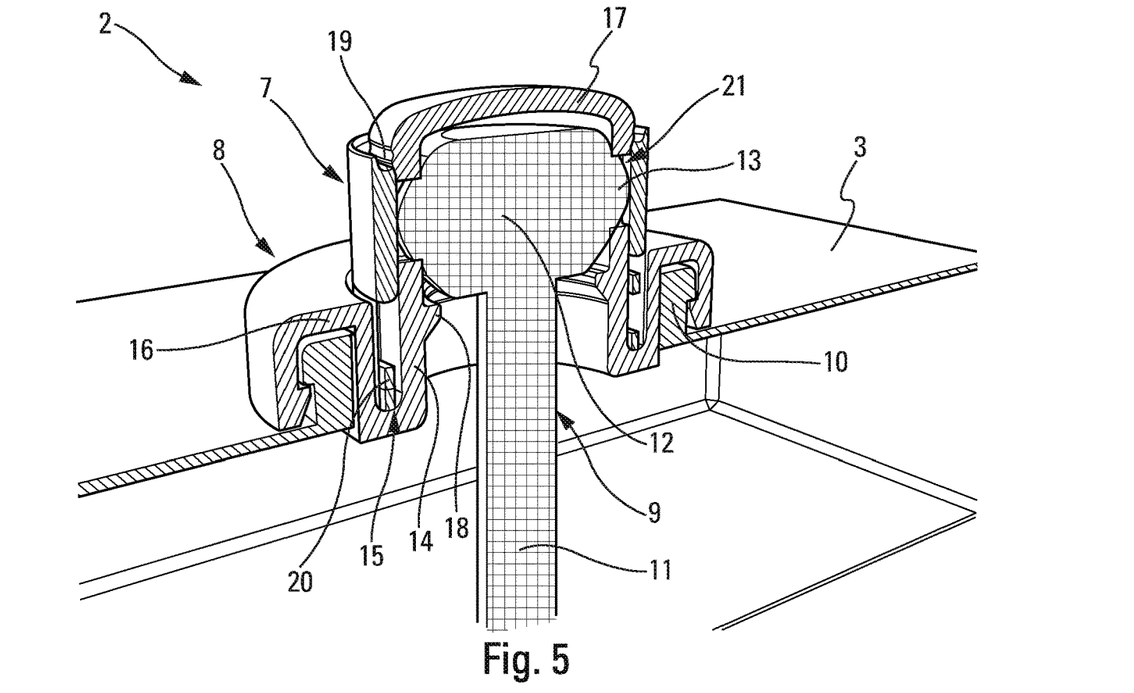
FIG. 5 is a cross-sectional and perspective view of a fixed part with the fret thereof in the upper protection position, mounted on a reservoir.

As illustrated in FIGS. 5 and 6, these means of protection against the evaporation of the product consist of a fret 7 that is movable in translation against spring means between an upper protection position facing the slits 21 of the base and a lower position providing free access for the nomadic element to the slits 21 for the nomadic element 1.

In FIG. 5, the fret 7 is in the upper position and covers the entire upper part of the sleeve 14 entirely so as to form a barrier against the evaporation of perfume through the slits 21. Better still, the cap 17 of the sleeve 14 includes a peripheral rim 19 against which the fret 7 abuts in the upper position, to ensure complete sealing between the base 8 and the fret 7. Thus, when there is no nomadic element 1 in position on the fixed part 2, the base 8 is completely sealed and perfume cannot diffuse.

More precisely, the spring means of the fret 7 consist of flexible tabs 20 resting on the bottom of a groove 15 formed between the sleeve 14 and the skirt 16 of the base 8. These flexible tabs 20 can take the form of a coil spring, or can simply correspond to a plurality of tabs 20 capable of bending under the effect of a stress. Any tab shape can be considered.

In FIG. 6, the fret 7 is in the lower position with free access of the nomadic element 1 to the slits 21. Indeed, under the effect of a stress applied to the fret 7, the tabs 20 bend and the fret 7 translates towards the bottom of the groove 15 until it is entirely hidden inside the groove 15. The slits 21 with projections 13 from the fixed porous body 9 are thus exposed, and diffuse perfume.

In FIG. 8, the fret 7 is in the upper position since the nomadic element 1 is at a distance from the fixed part 2. No perfume diffusion is therefore achieved at the fixed part 2.

In FIG. 7, the user puts the nomadic element 1 into place on the base 8 of the fixed part 2. During placement, the jewel 4 will apply a force on the fret 7 and will drive it in translation towards the lower position thereof. The nomadic element 1 is then in position all around the upper part of the sleeve 14 of the base 8, and the fixed porous body 9 is in contact with the mobile porous body 5, the transfer of perfume by capillarity thus takes place, as described above.

The nomadic element 1 can remain in place around the sleeve 14 because it is sized such that it applies a radial and axial friction against the sleeve 14, which is sufficient to resist the return force of the flexible tabs 20 of the fret 7. Indeed, the inner diameter of the jewel 4 is almost identical to the outer diameter of the sleeve 14 such that the nomadic element 1 can be put into place on the sleeve 14 by applying a gentle force. Furthermore, the crown 6 of the nomadic element 1 includes a slightly convex shape at the junction thereof between the peripheral wall thereof and the upper and lower lips thereof, that come into position under the peripheral rim 19 of the cap 17 of the sleeve 14, thus making it possible to better keep the nomadic element 1 in position on the base 8.

FIG. 9 shows a first possible configuration of a crown 6 belonging to the nomadic element 1. As described above, this crown 6 includes openings 23 and an upper lip 26 and a lower lip 27. The radial extension of the lips 26, 27 is sufficient to cover the thickness of the mobile porous body 5.

Figure 10:
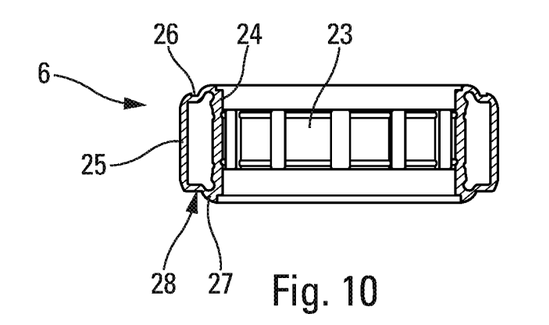
FIG. 10 represents a second possible configuration of a crown belonging to the nomadic element.

It could also be considered to extend these lips 26, 27 by a protection shield 25 that completely surrounds the mobile porous body 5, as illustrated in FIG. 10, to form a protection cage. In this case, an interstice 28 is formed between the shield 25 and the lower lip 27 in order to make it possible for the mobile porous body 5 to be inserted in the volume defined between the shield 25 and the peripheral wall of the crown 6. In this case, the mobile porous body 5 is entirely hidden behind the shield 25. The jewel 4 is entirely protected from the mobile porous body 5.

Figure 11:
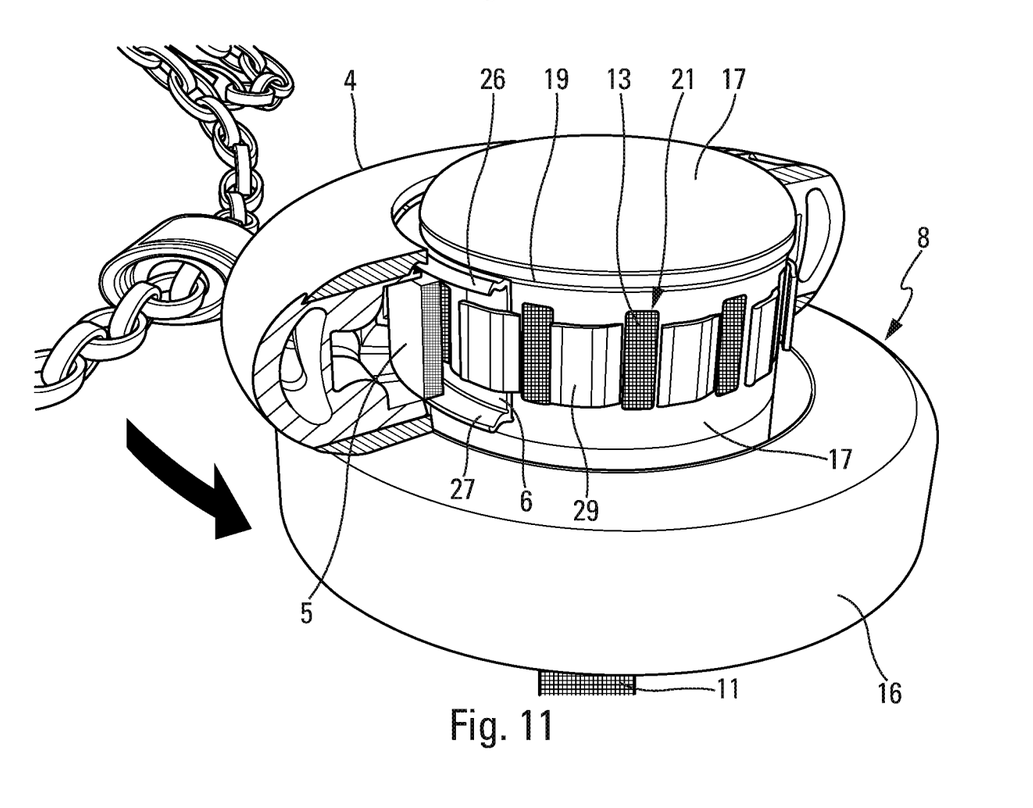
FIG. 11 is a perspective and partially cross-sectional view of a nomadic element mounted on a fixed part with the crown of the nomadic element fixed in the base of the fixed part.
Figure 16:
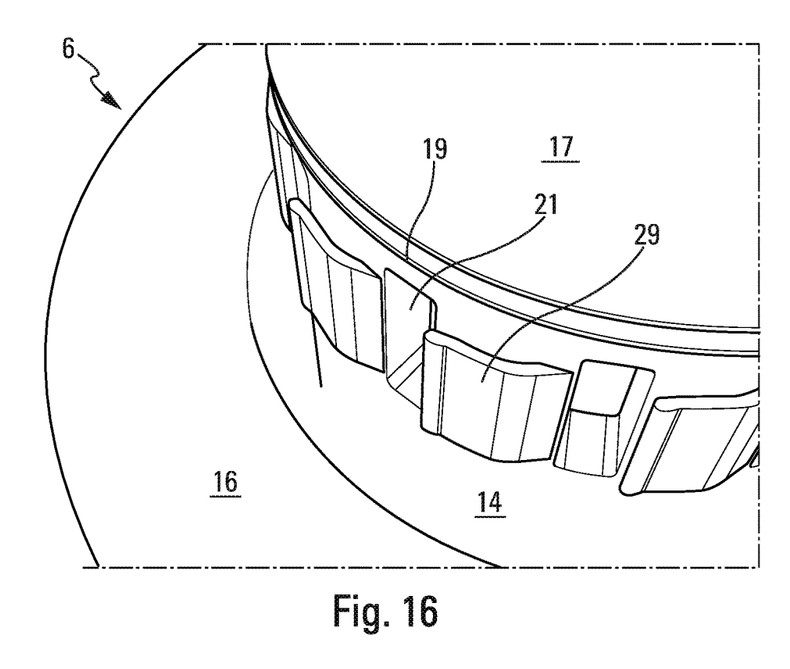
FIG. 16 is an enlarged, perspective view of a base of a fixed part.

When the mobile porous body 5 is replaced, the crown 6 of the nomadic element 1 attaches itself to the sleeve 14 of the fixed part 2, in order to be separated from the jewel 4, and that the replacement of the mobile porous body 5 can be done. For this, attachment tabs 29 are provided on the sleeve 14 of the base 8. These tabs 29 are illustrated in particular in FIGS. 11 and 16. More precisely, these tabs 29 extend tangentially from the external peripheral wall of the sleeve 14, and are all oriented in the same direction of rotation. Each tab 29 is placed between two adjacent slits 21. Each tab 29 is capable of penetrating inside an opening 23 in the crown 6 when the nomadic element 1 is in place on the fixed part 2 and the user rotates the nomadic element 1.

Figure 12:
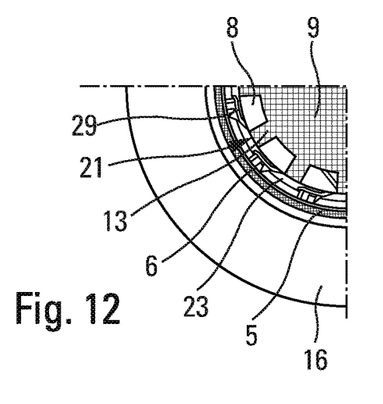
FIG. 12 is a transversal cross-sectional view of the diffusion device according to FIG. 7 with the crown of the nomadic element separated from the base of the fixed part.
Figure 13:
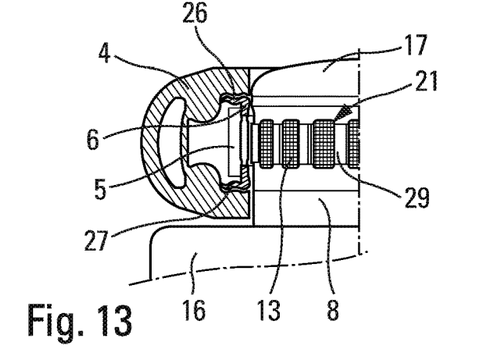
FIG. 13 is a longitudinal cross-sectional view of the diffusion device according to FIG. 7 with the crown of the nomadic element separated from the base of the fixed part.

In FIGS. 12 and 13, the nomadic element 1 is simply put into place and pushed onto the sleeve 14, for a conventional refilling of perfume by capillarity.

Figure 14:
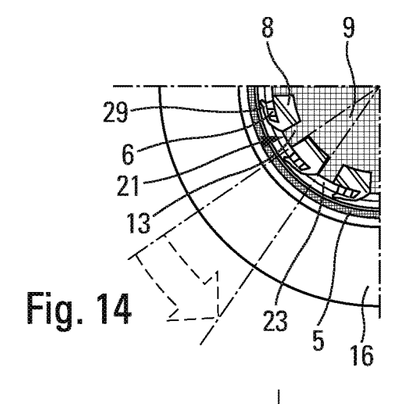
FIG. 14 is a transversal cross-sectional view of the diffusion device according to FIG. 11 with the crown of the nomadic element fixed to the base of the fixed part.
Figure 15:
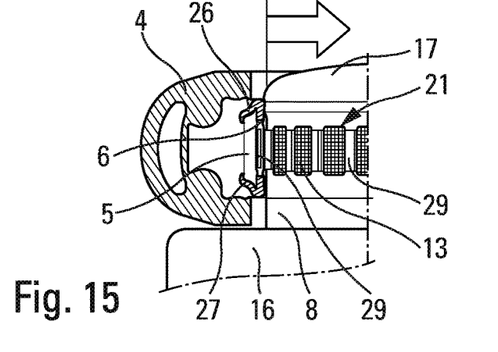
FIG. 15 is a longitudinal cross-sectional view of the diffusion device according to FIG. 11 with the crown of the nomadic element fixed to the base of the fixed part.

If the user wishes to replace the mobile porous element, for example because it is too old, all they need to do is to rotate the mobile element 1 with respect to the base 8 as indicated by the arrows on FIGS. 14 and 15. Thanks to this rotation, the tabs 29 penetrate inside the openings 23 in the crown 6, and the latter is thus secured to the sleeve 14. The user can then remove the jewel 4 alone with respect to the base 8. The crown 6 and the mobile porous body 5 remain attached to the base 8. The user can then easily remove the mobile porous body 5 from the crown 6 and implement another one. To secure the jewel 4 to the crown 6 again, it is sufficient to carry out the opposite operation, in other words to insert the jewel 4 again on the sleeve 14 via an axial translation movement, then to rotate the jewel 4 with respect to the base 8 in the opposite direction such that the tabs 29 are withdrawn from the openings 23 of the crown 6, and the crown 6 is thus once again engaged inside the jewel 4. The nomadic element 1 can then be withdrawn again completely from the base 8.

The same applies during first use of the mobile porous body 5. Indeed, at the first use, the crown 6 is secured to the sleeve 14 as illustrated in FIGS. 14 and 15, with the mobile porous body 5. The user can then choose the jewel 4 they prefer, and then put it into position and push it onto the sleeve 14. It is thus sufficient for them to rotate the jewel 4 in the opposite direction of the arrows so as to withdraw the tabs 29 from the openings 23 of the crown 6. The crown 6 and the mobile porous body 5 are then engaged inside the jewel 4, and the user can withdraw the entire nomadic element 1 from the base 8.

When the tabs 29 are completely engaged in the openings 23, the crown 6 thus tends to deform radially. Indeed, the crown 6 is made from a material that has elastic properties making it possible for it to deform elastically. In this case, by continuing their rotational movement, the user will deform the peripheral wall of the ring 6 radially inwards, given the attachment made with the tabs 29. This radial deformation will generate an angular deformation of the upper and lower lips 26 and 27, that will tend to move towards each other to close on the mobile porous body 5.

Optionally, the upper and lower lips 26 and 27 of the crown 6 have zones of weakness at the junction thereof with the peripheral wall of the crown 6. These zones of weakness make it possible to bend the lips 26, 27 so as to fold them even closer to the mobile porous body 5, as is illustrated in FIG. 15.

When the two lips 26, 27 are folded back, it is much easier for the user to remove the jewel 4 from the crown 6, the latter being secured to the sleeve 14 via the tabs 29.

The configurations shown in the figures mentioned are only possible examples of the invention that are in no way limitative, on the contrary the invention includes all variants of shapes and designs within the reach of a person skilled in the art.

Of note, the terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "includes", and/or "including," when used in this specification, specify the presence of stated features, integers, steps, operations, elements, and/or components, but do not preclude the presence or addition of one or more other features, integers, steps, operations, elements, components, and/or groups thereof.

As well, the corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

Having thus described the invention of the present application in detail and by reference to embodiments thereof, it will be apparent that modifications and variations are possible without departing from the scope of the invention defined in the appended claims as follows.

The invention claimed is:

1. A device for diffusion of a liquid product, comprising:
a reservoir;
at least one fixed part mounted on the reservoir, comprising:
   a base comprising at least one slit;
   a fixed porous body attached to the base and immersed in the reservoir, the fixed porous body comprising at least one projection extending through the at least one slit in the base;
   a spring; and a fret in movable translation with the spring between an upper protection position in which the fret covers the at least one slit and a lower position in which the fret does not cover the at least one slit;
a nomadic element, comprising:
a decorative structure; and
a mobile porous body housed in the decorative structure, wherein the mobile porous body is in contact with the at least one projection when the nomadic element is mounted on the at least one fixed part.

2. The device for diffusion of a liquid product according to claim 1, wherein the nomadic element further comprises a crown holding the mobile porous body and preventing any direct contact between the mobile porous body and the decorative structure.

3. The device for diffusion of a liquid product according to claim 1, wherein said base further comprises a sleeve closed by a cap at the top and open at the bottom and defining a housing for the fixed porous body, said at least one slit on a peripheral wall of the sleeve.

4. The device for diffusion of a liquid product according to claim 1, wherein said spring comprises a plurality of tabs.

5. The device for diffusion of a liquid product according to claim 1, wherein the nomadic element applies a force on the fret moving it to the lower position when the nomadic element is mounted on the at least one fixed part.

6. The device for diffusion of a liquid product according to claim 2, wherein the crown further comprises an upper attachment lip and a lower attachment lip, said upper attachment lip and said lower attachment lip having a radial extension sized to ensure that the mobile porous body does not contact the decorative structure.

* * * * *